United States Patent
Mirmiran

(10) Patent No.: US 11,241,556 B2
(45) Date of Patent: Feb. 8, 2022

(54) METHOD TO ACTIVATE AND CONTROL A CONDITIONING APPARATUS

(71) Applicant: De' Longhi Appliances S.r.l. con Unico Socio, Treviso (IT)

(72) Inventor: Roshanak Mirmiran, Treviso (IT)

(73) Assignee: DE'LONGHI APPLIANCES S.R.L. CON UNICO SOCIO, Treviso (IT)

( * ) Notice: Subject to any disclaimer, the term of this patent is extended or adjusted under 35 U.S.C. 154(b) by 274 days.

(21) Appl. No.: 16/553,291

(22) Filed: Aug. 28, 2019

(65) Prior Publication Data
US 2020/0069907 A1 Mar. 5, 2020

(30) Foreign Application Priority Data

Aug. 29, 2018 (IT) .................. 102018000008235

(51) Int. Cl.
*A61M 21/02* (2006.01)
*G16H 40/63* (2018.01)
*A61M 21/00* (2006.01)

(52) U.S. Cl.
CPC .......... *A61M 21/02* (2013.01); *G16H 40/63* (2018.01); *A61M 2021/0066* (2013.01); *A61M 2205/3368* (2013.01); *A61M 2230/06* (2013.01)

(58) Field of Classification Search
CPC ...... A61M 2205/3368; A61M 2230/06; A61M 21/02; A61M 2021/0066; A61B 5/4812; F24F 2120/14; F24F 11/80; F24F 11/66; F24F 2120/12; G16H 40/63
See application file for complete search history.

(56) References Cited

U.S. PATENT DOCUMENTS

| | | | |
|---|---|---|---|
| 2014/0316192 A1* | 10/2014 | de Zambotti | A61B 5/0205 600/28 |
| 2015/0105917 A1 | 4/2015 | Sasaki et al. | |
| 2018/0080673 A1 | 3/2018 | Yamaji | |

FOREIGN PATENT DOCUMENTS

| | | |
|---|---|---|
| CN | 105650815 A | 6/2016 |
| EP | 3093569 A1 | 11/2016 |
| JP | H09303842 A | 11/1997 |
| JP | 2003322383 A | 11/2003 |
| JP | 2012237501 A | 12/2012 |

OTHER PUBLICATIONS

"Relationship between Age and Heart Rate Variability in Supine and Standing Postures: A study of spectral analysis of Heart Rate." VK Yeragani, R Pohl, R Berger, R Balon, and K Srinivasan. Pediatric Cardiol 15: 14-20, 1994. (Year: 1994).*

* cited by examiner

*Primary Examiner* — Christine H Matthews
*Assistant Examiner* — Joshua Daryl D Lannu
(74) *Attorney, Agent, or Firm* — Panitch Scwarze Belisario & Nadel LLP

(57) ABSTRACT

A conditioning apparatus is provided with a control and command unit which can be activated remotely using an electronic device. A method to activate and control the conditioning apparatus includes regulating the functioning parameters of the conditioning apparatus at least as a function of a state of wakefulness or sleep of a user.

12 Claims, 2 Drawing Sheets

METHOD TO ACTIVATE AND CONTROL A CONDITIONING APPARATUS

CROSS-REFERENCE TO RELATED APPLICATION

This application claims priority under 35 U.S.C. § 119(b) to Italian Application No. 102018000008235, filed Aug. 29, 2018, the disclosure of which is incorporated herein by reference in its entirety.

FIELD OF THE INVENTION

The present invention concerns a method to activate and control a conditioning apparatus, which allows to regulate the thermal conditions of a room in order to optimize the comfort and well-being for a user when he/she goes to sleep and/or while he/she is sleeping, so as to optimize the quality of the user's sleep and rest.

BACKGROUND OF THE INVENTION

Sleep is a periodic state of more or less complete suspension of consciousness and will, indispensable for restoring the physical and mental efficiency of an individual, during which the nervous system is inactive, the eyes are closed, the postural muscles are in a relaxed state, and consciousness is practically suspended.

It is known that during sleep there is an alternation of phases of more or less deep sleep that are repeated cyclically, between an active sleep phase, also called REM phase (Rapid Eye Movement) and a quiet sleep phase, generally referred to as the NREM phase (Non-Rapid Eye Movement) comprising four stages of sleep that are progressively deeper. A complete sleep cycle is generally characterized by progression from the first to the fourth stage before reaching the REM phase and starting again. During sleep, the duration of the REM phases progressively tends to increase at the expense of the NREM phases, which generally occur at the beginning of the sleep state, and whose deepest stages strongly influence the restoration of the organism.

It is known that the quality of the sleep plays an important role in an individual's physical and mental health, and can be influenced by various factors including, for example, age, illnesses, alcohol use/abuse, stimulants, or psychotropic drugs, style of life and diet.

The quality of sleep also depends on the climatic conditions of the room in which one sleeps. Temperatures that are too low, or too high, can negatively affect rest, and in particular can prevent an individual from reaching the deeper sleep phases, which allow to obtain a better rest.

It is also known that the body temperature of an individual varies during the course of a day, according to a periodic trend, in which the maximum temperature value is reached toward the late afternoon and the minimum value during the night, just before the time one awakes. The sleep state generally begins during the period when the body temperature begins to decrease, which is due to a reduction in heat production and an increase in heat losses.

Furthermore, the trend of an individual's body temperature is correlated to the quantity of deep sleep. In other words, an individual with a lower body temperature can achieve a deeper sleep, which ensures better rest and optimal recovery of physical and mental efficiency.

In order to regulate in an appropriate manner at least the climatic conditions of a room, it is known to use ventilation or conditioning apparatuses, suitable to generate a flow of air at a desired temperature, possibly regulating the flow rate and humidity thereof.

For example, ventilation or conditioning apparatuses are known in which a user can define his/her own temperature, humidity and/or air speed settings. These known apparatuses also allow to set their activation at a predetermined time or with a defined delay time interval. These apparatuses can therefore be programmed to modify their functioning conditions based on an estimated timing correlated to whether the user is asleep or awake.

Because of this, known solutions do not allow to optimize the effective quality of a user's sleep and therefore increase his/her comfort and physical well-being.

Other solutions are also known which provide to monitor the sleep of a user in order to regulate the conditioning apparatus accordingly.

Document US-A-2018/080673 discloses a method to control a conditioning apparatus which provides to detect the motion of a user by means of Doppler sensors. One disadvantage of this known solution is that it requires to position one or more sensors in correspondence with the area occupied by the user when he/she is sleeping and therefore it is not very versatile.

Document JP-A-2003 322383 refers to a control system for a conditioning apparatus which provides to modify the functioning of the apparatus based on a sleeping state of a sleeping user detected by means of the internal pressure of an air mattress on which the user lies. Also this solution is not very versatile, since it requires to connect suitable sensors to the mattress and it is also necessary for the user to position himself on the mattress itself.

From US-A-2015/105917 a control method for controlling a conditioning apparatus is also known which provides to detect the body-movements values of a user during sleep by means of an accelerometer or eventually the heartbeat rates and display the detected data on a user interface so that the user can modify the setting temperature values for different time slots in the sleeping period based on the movements previously detected in such time slots.

Document JP-A-H09 303842 relates to an air conditioner capable of providing comfortable air temperature conditions for users who are not able to select comfortable air conditions autonomously, such as infants and elderly people. This air conditioner comprises a sensor to monitor a physiological parameter of the user during sleep, thermal environmental detection means to detect temperature and humidity conditions, and control means which control an operation state of the air conditioner based on detected data and based on previously detected and stored data.

Other control systems are known also from EP-A-3 093 569, JP-A_2012 237501, CN-A-105650815, which provide to detect a user's parameter during sleep, so as to determine different sleep states of the user's sleep, more or less deep, and to regulate accordingly the conditioning apparatus.

This known solutions are intended to detect the movements and the physiological parameters of a user while he/she is sleeping and do not provide the possibility to select a determinate functioning mode for the conditioning apparatus which can be automatically activated on the basis of the detection of a state of the user.

Moreover, these solutions do not provide to monitor the user's state even before he/she goes to sleep.

One purpose of the present invention is to provide a control method which automatically activates a selected functioning mode of the conditioning apparatus suitable to optimize the quality of the user's sleep when a user goes to rest, or possibly to sleep.

One purpose of the present invention is also to provide a method to activate and control a conditioning apparatus which determines the starting of the set functioning mode based on the detection of a determined resting position of the user.

One purpose of the present invention is also to provide a method to activate and control a conditioning apparatus which improves comfort for the user in sleep and rest situations more effectively than known solutions.

Another purpose of the present invention is to provide a method to activate and control a conditioning apparatus which allows to regulate the conditions of the room in an adaptive manner during the user's sleep phases.

The Applicant has devised, tested and embodied the present invention to overcome the shortcomings of the state of the art and to obtain these and other purposes and advantages.

SUMMARY OF THE INVENTION

The present invention is set forth and characterized in the independent claim, while the dependent claims describe other characteristics of the invention or variants to the main inventive idea.

Embodiments described here concern a method to activate and control a conditioning apparatus that provides to modify the functioning parameters of the latter at least as a function of a standing or lying position of a user, correlated to a state of wakefulness or sleep of the user.

The control method according to the invention provides in particular to select a functioning mode of a conditioning apparatus that provides to perform a control function of the temperature in the time while the user is resting, or possibly sleeping, so as to keep the room temperature inside predefined ranges of values.

According to one aspect of the invention, the method provides to monitor the state of wakefulness or sleep of a user, and in particular a standing or lying position, possibly correlated to a state of wakefulness or sleep, and to activate the functioning mode selected, that is, to start the temperature control function when a variation is detected in the user's state or position.

In particular, the method according to the invention provides to activate the functioning mode selected when a lying position of the user is detected, which can be used as an indication of the fact that the user is lying down in bed and is therefore going to sleep.

According to some embodiments, the method provides to detect the heartbeat of a user by means of a device which can be worn by a user and to determine the lying position of the user based on the variation in frequency of the detected user's heartbeat.

The method according to the invention therefore provides to monitor the state and the heartbeat of the user also before the user goes to bed, substantially from the same moment when a specific functioning mode for the night hours and sleep is selected.

In other words, according to the method of the present invention, a user can select the specific functioning mode for the night hours and sleep at any moment of the day, continuing to then carry out his/her normal activities. In any case, the functioning mode selected is activated and starts its function when the user prepares to go to sleep, and lies down, for example in bed.

In any case, the specific functioning mode is activate as soon as a lying position of the user has been detected, and then not necessarily when the user goes to bed, and independently whether he/she lies in a determined bed or in a given area of the room.

Moreover, thanks to the automatic activation of the specific functioning mode as soon as it is detected that the user is in a laying position, the method allows to supply comfortable thermal conditions which can promote the sleep of a user, in particular if the user has difficulties in falling asleep.

According to other embodiments, in order to detect the lying condition of the user the method also provides to consider inertial parameters corresponding to movements of the user, detected, for example, by means of accelerometers or gyroscopes.

According to some embodiments, the execution of the control function of the temperature provides to initially set a predefined minimum temperature value, so as to lower the room temperature in the moment in which the user lies down.

In this way, during the initial sleeping phase, when the body temperature of the user is highest, the room temperature is brought to a minimum value, thus helping the user to reach a deep sleep phase.

The method according to the invention also provides to keep the temperature constant at the minimum value for a defined period of time, correlated to the length of the deep sleep stages of the user, that is, the period of time in which a user generally tends to sweat or to be more negatively affected by the higher temperatures.

Subsequently the method according to the invention provides to set an intermediate temperature value, keeping it constant for a second period, and then gradually increasing the temperature to obtain a desired maximum temperature in correspondence to the time when the user wakes up.

In this way, the slowly increasing temperature compensates for the user's progressive and gradual loss of temperature, guaranteeing at every moment a high degree of comfort.

BRIEF DESCRIPTION OF THE DRAWINGS

These and other characteristics of the present invention will become apparent from the following description of some embodiments, given as a non-restrictive example with reference to the attached drawings wherein.

To facilitate comprehension, the same reference numbers have been used, where possible, to identify identical common elements in the drawings. It is understood that elements and characteristics of one embodiment can conveniently be incorporated into other embodiments without further clarifications.

DETAILED DESCRIPTION OF SOME EMBODIMENTS

Figure 1:
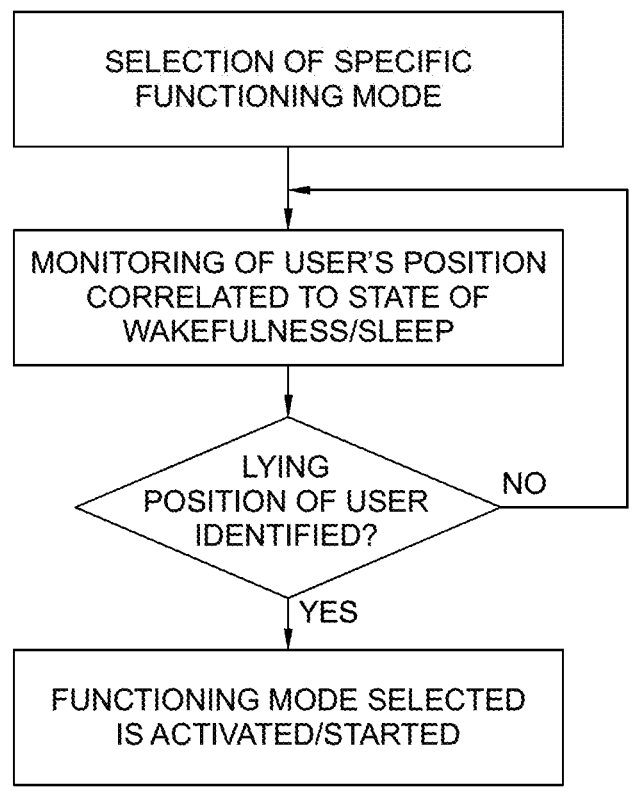
FIG. 1 is a block diagram that shows some steps of the method according to the invention.
Figure 2:
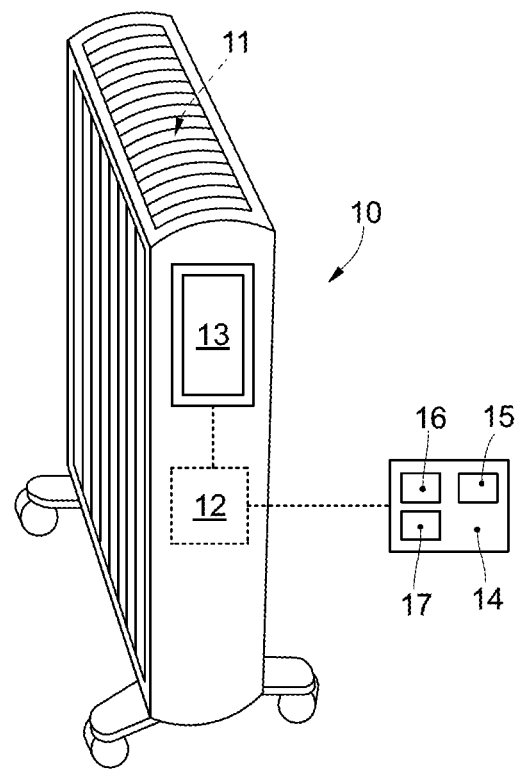
FIG. 2 is a schematic view of an example of a conditioning apparatus in which the method according to the invention can be implemented.

Embodiments described here concern a method to activate and/or control a conditioning apparatus 10 which provides to activate a specific function of controlling the temperature in the time when the user goes to sleep, to maintain the temperature values inside predefined intervals while the user is sleeping.

According to some embodiments, the conditioning apparatus 10 can comprise in a known way a conditioning device 11, configured to heat, cool and/or dehumidify a flow of air, and possibly a ventilation device, not shown, configured to generate a flow of air and direct it toward the conditioning device 11 and toward the outside of the apparatus 10.

The conditioning apparatus 10 can also comprise, in a known manner, one or more sensor devices, not shown, suitable to measure the values of one or more characteristics and quantities, among which, for example, temperature, pressure, humidity, speed of a flow of air, or other.

The conditioning apparatus 10 can be of the mobile or fixed type, for example installed and/or integrated in the walls of a room to be conditioned. By way of example, the conditioning apparatus 10 can be an oil radiator, a heat pump, a convector heater, a fan convector heater, or a similar apparatus.

According to some embodiments, the conditioning apparatus 10 comprises a control and command unit 12 configured to regulate its operation on the basis of predefined parameters, or set by a user.

For this purpose, the conditioning apparatus 10 can comprise a user interface 13, connected to the control and command unit 12, by means of which the user can set the desired temperature values, possibly defined for specific time intervals, and/or the speed of the outgoing flow of air, or select one of the different predefined functioning modes.

The control unit 12 and/or the user interface 13 can be provided with data communication devices of a known type suitable to receive and/or transmit data in wireless mode.

According to some embodiments, the control unit 12 can also be commanded remotely by an electronic device 14 on which a dedicated software app is installed.

The electronic device 14 can be selected from a smartphone, a smartwatch, or other similar device, provided with a processing unit 16 and a communication interface 17 suitable to communicate wirelessly with the control unit 12 and/or the user interface 13 of the conditioning device 10.

According to some embodiments, the electronic device 14 comprises, or is connected to, a heartbeat detection device, for example a heart rate monitor configured to detect the number of heartbeats per minute (HR—Heart Rate), that is, a user's cardiac frequency.

According to some embodiments, the heartbeat detection device 15 is integrated into the electronic device 14, for example in the case of a smartwatch, or it can be integrated into an accessory wearable by a user, for example a chest band, a bracelet, or suchlike, and be provided with data communication means, suitable to communicate wirelessly with the electronic device 14.

The method to activate and control the conditioning apparatus 10 according to the invention provides to select a specific functioning mode of the conditioning apparatus 10, and in particular a functioning mode suitable to perform a regulation of the temperature during the sleep period of a user, based on predefined parameters.

According to some embodiments, the predefined parameters can be pre-set, and memorized in the control and command unit 12, or can be inserted by a user through the user interface 13 and/or through the electronic device 14 provided with the dedicated software app.

According to some embodiments, the predefined parameters can comprise minimum and maximum temperature values, the scheduled time for the user to wake up, or other.

When the specific functioning mode is selected, the method according to the invention provides to monitor a user's state or position and activate or start the execution of said functioning mode when a variation of this state and/or position is detected.

According to some embodiments, the method provides to activate the specific functioning mode when a user's lying position is detected, that is, a variation in the user's position from standing, or possibly sitting, to lying.

According to some embodiments, the method according to the invention provides to use the frequency of a user's heartbeat as an indicator of his/her upright/lying position, which can be detected by the heartbeat detection device 15.

The user can therefore set the specific functioning mode suitable to regulate the conditioning apparatus 10 during the sleeping period in every moment of the day, which will be activated ad made to start automatically by the control and command unit 12 when the frequency of the detected heartbeat is indicative of a lying position of the user.

According to some embodiments, to identify the lying position, the method provides to compare the data detected on each occasion in a determined instant with data detected in preceding instants, so as to identify possible variation in the heartbeat's trend.

According to some embodiments, the method provides to identify a peak in the trend of a user's heart rate, indicative of a change in his/her position and to verify whether, downstream of the peak detected, the user has assumed or not a lying position.

Figure 3:
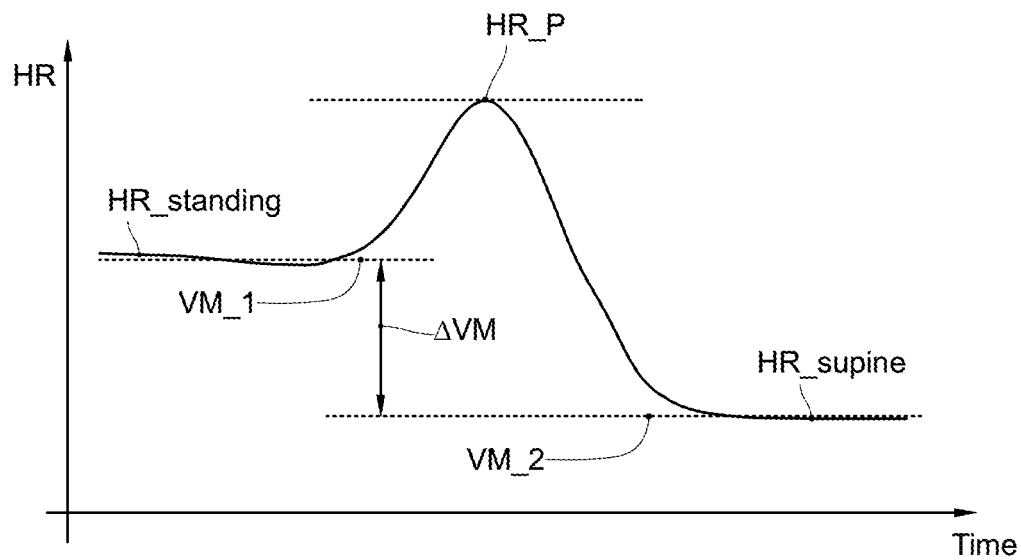
FIG. 3 is a graph showing the trend of the frequency of the user's heart beat when he/she passes from a upright or standing position to a lying position.

FIG. 3 shows a typical trend of an individual's heart rate when he/she varies his/her posture from an upright/standing position to a lying position.

In the case of an individual who is in general good health, when he/she is in the upright/sitting position, his/her heart rate is around a first average frequency HR_standing; when the individual is in the lying position, his/her heart rate is around a second average frequency HR_supine, lower than the first average frequency HR_standing.

As can be seen in FIG. 3, in the transition zone between the upright position and the lying position, that is, between the first average value in the upright position HR_standing and the second average value in the lying position HR_supine, the heart rate reaches a maximum peak value HR_P.

According to some embodiments, in order to identify the user's lying position, and to determine when to activate the temperature control function associated with the selected functioning mode, the method according to the invention provides to automatically and periodically perform a detection algorithm.

The detection algorithm can be performed by a suitable processing unit 16, for example the processing unit 16 of the electronic device 14.

It is not excluded, however, that the algorithm can be executed by the control unit 12 of the conditioning apparatus 10 on the basis of the data received from the electronic device 14.

According to some embodiments, the method provides to start the execution of the detection algorithm when the specific functioning mode is selected.

An example of an algorithm that can be used to identify the user's lying position will be described below. It is understood, however, that the present invention can provide to use other algorithms or other types of processing as an alternative or in addition to the algorithm described, to identify the user's lying position and determine when to activate the desired functioning mode.

According to some embodiments, the algorithm comprises a step of identifying the frequency peak, and a step of verifying the position assumed by the user after the peak identified.

According to some embodiments, the algorithm comprises the sampling and periodic recording of frequency values HR of the user's heartbeat according to a defined period.

The HR values of the heartbeat in particular can be detected by means of the heartbeat detection device 15 substantially continuously starting form the instant in which the specific functioning mode is selected.

By way of example, the period can last t seconds, where t can be a predefined number, for example correlated to the sampling frequency of the detection device 15. By way of example, in the case of a functioning frequency of about 0.2 Hz, the period will be about 5 s.

According to some embodiments, the algorithm also comprises a step of memorizing the HR(i) values recorded in a plurality of successive sampling instants, and ordering them in a vector, or matrix, in a progressive manner from an initial start instant of the algorithm where i=1.

According to possible solutions, the algorithm provides to process the data recorded and ordered to identify at least a peak in the frequency trend of the user's heartbeats.

According to some embodiments, the algorithm provides to process the values recorded in real time, while they are being detected.

According to other variants, the algorithm can provide to create a mobile window and process the data after having memorized them.

According to some embodiments, the algorithm provides to calculate, at each sampling instant i, the difference ΔHR(i) between the heart rate value at the time of sampling considered HR(i) and the heart rate value recorded in the previous sampling instant HR(i−1).

According to some embodiments of the algorithm, the following formula can be used:

$$\Delta HR(i) = HR(i) - HR(i-1).$$

According to some embodiments, the algorithm also provides to calculate the sum of the difference values ΔHR(i) from the initial instant the algorithm is started, that is, from the selection of the specific functioning mode, up to a current instant, and to compare this sum with a first reference value Vref_1.

The first reference value Vref_1 can correspond to the difference between the peak value HR_P and the first average value in the upright position HR_standing.

The first reference value Vref_1 can be chosen according to the sampling frequency of the detection device 15. By way of example, the first reference value Vref_1 can be equal to or greater than 5 heartbeats/min, for example 15 heartbeats/min, 20 heartbeats/min.

According to possible implementations of the algorithm, when it occurs that:

$$\sum_{i}^{k} \Delta HR(i) > Vref\_1;$$

that is, the sum of the difference values ΔHR(i) calculated for i that goes from 1 to a current sampling instant k is greater than the first reference value Vref_1, then the presence of a frequency peak HR_P is identified in a neighborhood of the sampling instant k considered.

After the frequency peak HR_P has been detected, the algorithm provides to verify if it corresponds to a variation in the position of the user from an upright position, correlated to a waking state, to a lying position, related to a user's potential sleep state.

According to some embodiments, in order to perform the verification, the algorithm provides to consider all the values HR(i) of the heartbeats detected for each instant i comprised between the instant of selection of the control function (corresponding to i=1) and an instant preceding the one in which the peak was identified (for example preceding i=k) and to calculate a first average value VM_1.

According to some embodiments, the algorithm also provides to consider the values HR(i) of frequency of the heartbeats measured after the instant in which the peak has been detected (for example following i=k+1) and to calculate a second average value VM_2.

Finally, the algorithm according to the invention provides to calculate the difference in the averages ΔVM between the first average value VM_1 and the second average value VM_2, and to compare it with a second reference value Vref_2.

According to some embodiments, the second reference value Vref_2 can be chosen according to the sampling frequency of the heartbeat detection device 15. By way of example, the second reference value Vref_2 can be greater than 5 heartbeats/min, such as 15 heartbeats/min, 20 heartbeats/min, similar to the first reference value Vref_1, or even higher than it.

According to some embodiments, in the case where the difference in the averages ΔVM exceeds the second reference value Vref_2, that is:

$$\Delta VM = VM\_1 - VM\_2 > Vref\_2,$$

the user's lying position is identified.

When the user's lying position is recognized, the method according to the invention provides to activate and start the selected functioning mode.

In particular, the method provides to send an activation signal to the control and command unit 12 of the conditioning apparatus 10, which in turn commands the functioning of the apparatus 10 to perform the temperature control function provided by the functioning mode selected.

According to some embodiments, the average value in the upright position HR_standing, the average value in the lying position HR_supine and the peak value HR_P used by the algorithm can be characteristic values of the individual user, for example detected with an initial setting step of the heartbeat detection device 15 and/or the dedicated software app provided on the electronic device 14 and/or in the control and command unit 12.

Figure 4:
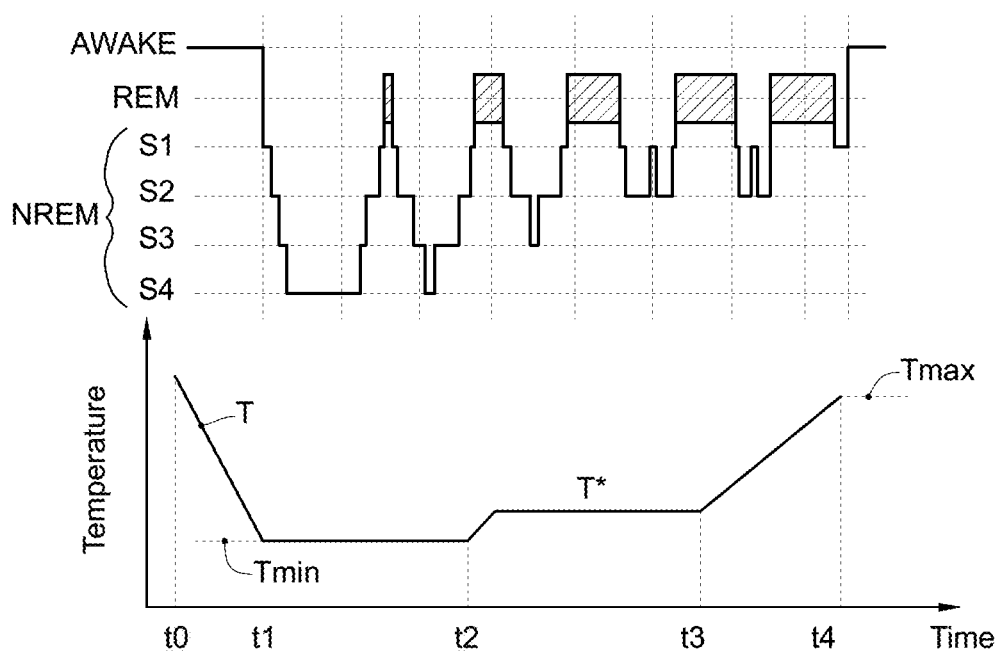
FIG. 4 is a graph in which the variations of the temperature settings of the conditioning apparatus are shown as a function of the different sleeping phases of a user according to embodiments of the present invention.

In the upper part of FIG. 4 the phases of a user's sleep are schematically shown, which alternate in successive cycles between NREM sleep phases, more frequent at the beginning of sleep, which become gradually shorter, and REM sleep phases which, on the contrary, tend to increase progressively with the passing of the hours of sleep.

The lower part of FIG. 4 shows a possible trend of the temperature regulated according to the method of the present invention, which allows to optimize the user's sleep, and in particular to facilitate drowsiness and to guarantee a thermal comfort suitable to facilitate the achievement of the deeper phases of NREM sleep.

According to some embodiments, at the instant t0, that is, at the start of the functioning mode to regulate the temperature during sleep, the method according to the invention provides to lower the temperature T to a minimum value Tmin.

The minimum temperature value Tmin can be set by the user, or it can be a predefined value on the basis of tables or parameters memorized in the control unit 12, for example obtained by means of analysis tests performed in the laboratory, or reported in scientific articles, or possibly calculated according to the room temperature.

According to some embodiments, the minimum temperature value Tmin can be comprised between about 15° C. and about 20° C., preferably between about 16° C. and about 19° C.

The temperature T will therefore begin to fall starting from an initial instant t0 corresponding substantially to when the user has assumed the lying position, until it settles around the minimum value Tmin, in a first instant t1. This contributes to lowering the body temperature of the user, which tends physiologically to decrease in the passage between the waking state and the sleeping state, and the user can then fall asleep more easily and more quickly.

According to some embodiments, the method according to the invention provides to keep the temperature T constant at the minimum value Tmin for a predetermined time interval, up to a second instant t2, in particular until the end of the deepest sleep states of the NREM phase.

According to some embodiments, the second instant t2 can be pre-set and memorized in the control and command unit 12, as a time interval with respect to the activation instant t0, or it can be a value entered by a user, or again, an estimated value based on one or more parameters such as age of the user, seasonal weather conditions, or other parameters.

According to some embodiments, in the second instant t2, that is at the end of the sleep cycles involving the NREM phase, the method according to the invention provides to set an intermediate temperature value T*, higher than the minimum value Tmin.

According to possible solutions, the intermediate value T* can be slightly higher than the minimum value Tmin, for example 1°-2° C. higher. The intermediate value T* can also be a pre-set value, inserted by the user, or determined according to one or more parameters.

Subsequently, the method according to the invention provides to keep the temperature T constant at the intermediate value T* for a defined period of time, up to a third instant t3, and then progressively increases the temperature T until reaching a maximum temperature value Tmax in proximity to the time the user wakes up.

According to some embodiments, the maximum value Tmax can be set by the user, or it can be a predefined value, or possibly calculated as a function of the room temperature.

According to some embodiments, the third instant t3 can be pre-set and memorized in the control and command unit 12 as a time interval from the activation instant t0, or from the second instant t2, or it can be calculated based on the time set for the user to wake up, or based on other parameters.

The method according to the invention therefore allows to regulate the temperature T in a way correlated to the phases of the user's sleep, optimizing his/her sensation of comfort and well-being and therefore the overall quality of sleep and rest.

According to some embodiments, the method according to the invention can also provide to detect a user's possible movements by means of an accelerometer, or other similar device at defined sampling instants, so as to verify whether he/she is actually sleeping.

According to some embodiments, the data detected by the accelerometer can be used as further verification of a user's lying position and/or sleep state.

According to possible variant embodiments, the data detected by the accelerometer can be used to further regulate the temperature supplied by the conditioning apparatus 10 as a function of the actual sleep cycle experienced by the user, for example on the basis of the alternation of successive cycles of REM and NREM phases.

It is clear that modifications and/or additions of parts can be made to the method to activate and control a conditioning apparatus 10 as described heretofore, without departing from the field and scope of the present invention.

It is also clear that, although the present invention has been described with reference to some specific examples, a person of skill in the art shall certainly be able to achieve many other equivalent forms of method to activate and control a conditioning apparatus, having the characteristics as set forth in the claims and hence all coming within the field of protection defined thereby.

The invention claimed is:

1. A method to activate and control a conditioning apparatus, in which the conditioning apparatus is provided with a control and command unit able to be activated remotely by an electronic device, the method providing to regulate functioning parameters of said conditioning apparatus at least as a function of a state of wakefulness or sleep of a user, wherein the method comprises:

selecting a specific functioning mode of said conditioning apparatus that performs a control function of a temperature in the time that the user is sleeping, until a time expected for the user to wake up, so as to keep a room temperature inside predefined ranges of values associated with a sleeping state of said user;

monitoring the a frequency of heartbeat values (HR(i)) of the user by a heartbeat detection device which can be worn by the user, integrated with and/or connected to said electronic device;

identifying a standing or lying position of the user, respectively correlated to the state of wakefulness or sleep, by processing frequency data of the heartbeat values (HR(i)) detected by the heartbeat detection device by a detection algorithm; and activating the functioning mode selected and commanding said conditioning apparatus for starting the temperature control function after detecting the standing or lying position of the user.

2. The method as in claim 1, wherein the frequency of the heartbeat values of the user is detected substantially continuously starting from an instant in which said specific functioning mode is selected.

3. The method as in claim 1, wherein said detection algorithm is started substantially from an instant in which said specific functioning mode is selected.

4. The method as in claim 1, wherein in order to identify said lying position of the user, detected frequency values of the heartbeat values (HR(i)) are memorized and a frequency value detected in a determined instant is compared with frequency values detected in preceding instants.

5. The method as in claim 1, wherein in order to detect said lying position of the user, the detection algorithm is automatically and periodically performed, the detection algorithm comprising a step of identifying a frequency peak (HR_P) of the heartbeat values in a trend of the heartbeat values of the user, and a step of verifying a position assumed by the user after the frequency peak is identified.

6. The method as in claim 5, wherein the step of identifying the frequency peak (HR_P) comprises:
   a step of sampling and periodic recording of the frequency values (HR(i)) of the heartbeat values of the user in a defined period;
   a step of memorizing and ordering the values recorded in a vector or matrix, progressively from an initial instant when the detection algorithm is started; and
   a step of processing the values (HR(i)) recorded.

7. The method as in claim 6, wherein said processing step of the recorded values (HR(i)) comprises:
   calculating, for each of a plurality of sampling instants, a difference (ΔHR(i)) between a value of cardiac frequency in a sampling instant considered, and a value of cardiac frequency recorded in a previous sampling instant.

8. The method as in claim 7, wherein said processing step of the recorded values (HR(i)) further comprises:
   calculating a sum of the difference (ΔHR(i)) in values from an initial instant when the algorithm is started, until a current instant; and
   comparing said sum with a first reference value (Vref_1).

9. The method as in claim 8, wherein said step of verifying the position assumed by the user after the frequency peak (HR_P) is identified comprises:
   considering values (HR(i)) of frequency of the heartbeat values detected for each of a plurality of sampling instants comprised between an instant when the control function is selected, and a sampling instant prior to an instant in which said frequency peak (HR_P) was identified and to calculate a first average value (VM_1) thereof;
   considering the values (HR(i)) of frequency of the heartbeats detected after the instant when said frequency peak (HR_P) was identified and to calculate a second average value VM_2) thereof; and
   calculating a difference in the averages (AVM) between said first average value (VM_1) and said second average value (VM_2) and comparing the calculated difference in the averages with a second reference value (Vref_2).

10. The method as in claim 1, wherein when said functioning mode is started, after detection of said lying position of the user, the temperature is lowered to a minimum value (Tmin) and said temperature is kept constant at said minimum value (Tmin) for a predetermined period of time, until a second switching instant (t2) correlated to an estimated duration of deep sleep stages of said user, a duration of said period of time being defined based on graphs or tables memorized or determined based on one or more parameters supplied by the user.

11. The method as in claim 10, wherein in said second instant (t2), an intermediate temperature value (T*) is set, higher than said minimum value (Tmin), then said temperature is kept constant at said intermediate value (T*) for a defined period of time, until a third instant (t3), and then said temperature is progressively increased until a maximum temperature value (Tmax) is reached in proximity to said time expected for said user to wake up.

12. The method as in claim 1, wherein one or more of the following parameters are initially set: predefined temperature values, reference values (Vref_1, Vref_2) correlated to average values of the frequency of the heartbeat values of the user in an upright position (HR_standing) and in the lying position (HR_supine), expected wake-up time or hour.

* * * * *